United States Patent [19]

Kaiser et al.

[11] Patent Number: 4,810,811

[45] Date of Patent: Mar. 7, 1989

[54] DOPAMINE-BETA-HYDROXYLASE INHIBITORS

[75] Inventors: Carl Kaiser, Haddon Heights; Lawrence I. Kruse, Haddonfield, both of N.J.

[73] Assignee: SmithKline Beckman Corporation, Philadelphia, Pa.

[21] Appl. No.: 88,773

[22] Filed: Aug. 24, 1987

Related U.S. Application Data

[62] Division of Ser. No. 700,234, Feb. 11, 1985, Pat. No. 4,707,488.

[51] Int. Cl.$^4$ ............................................. C07C 155/08
[52] U.S. Cl. .................................................. 558/235
[58] Field of Search ........................................ 558/235

[56] References Cited

U.S. PATENT DOCUMENTS 3,202,572  8/1965  Werres et al. .................. 558/235

OTHER PUBLICATIONS

Chem. Abstracts, vol. 83 (No. 5) Abst. No. 83:42957m Aug. 4, 1975.

Primary Examiner—Mary C. Lee
Assistant Examiner—Robert C. Whittenbaugh
Attorney, Agent, or Firm—Stuart R. Suter; Alan D. Lourie; Janice E. Williams

[57] ABSTRACT

The compounds of this invention are 1-phenylalkyl-2-mercaptotetrazole compounds which are dopamine-$\beta$-hydroxylase inhibitors.

4 Claims, No Drawings

DOPAMINE-BETA-HYDROXYLASE INHIBITORS

This is a divisional of pending application Ser. No. 700,234 filed Feb. 11, 1985 now U.S. Pat. No. 4,707,488.

This invention relates to inhibitors of dopamine-β-hydroxylase.

In the catecholamine biosynthetic pathway, tyrosine is converted in three steps to norepinephrine (NE). Intermediates are dihydroxyphenylalanine (DOPA) and dopamine (DA). The latter is hydroxylated to norepinephrine by dopamine-β-hydroxylase (DBH) in the presence of oxygen and ascorbic acid.

Inhibition of catecholamine activity has been found to decrease hypertension. See, for example, Matta et al., *Clin. Pharmacol. Ther.* 14, 541 (1973), and Teresawa et al., *Japan Circ. J.* 35, 339 (1971). Weinshilboum, *Mayo Clin. Proc.* 55, 39 (1980), reviews compounds which inhibit catecholamine activity by interfering with adrenergic receptors. Alternatively, the catecholamine biosynthetic pathway can be suppressed at any of the three steps, resulting in decreased levels of NE. In addition to decreasing hypertension, inhibitors of NE synthesis are active as diuretics, natriuretics, cardiotonics and vasodilators. Inhibition of DBH activity can have the added advantage of increasing levels of DA, which as reported by Ehrreich and Korduba, "New Antihypertensive Drugs," Spectrum Publishing, 1976, pp. 409-432, has been found to have selective vasodilator activity at certain concentrations.

DBH inhibitors have also been shown to reduce or prevent formation of gastric ulcers in rats by Hidaka et al., "Caetcholamine and Stress," edit. by Usdin et al., Permagon Press, Oxford, 1976, pp. 159-165 and by Osumi et al., *Japan J. Pharmacol.* 23, 904 (1973).

A number of DBH inhibitors are known. These are generally divided into two classes, namely, metal chelating agents, which bind to copper in the enzyme, and phenethylamine analogues. Rosenberg et al., "Essays in Neurochemistry and Neuropharmacology, Vol. 4," edit. by Youdim et al., John Wiley & Sons, 1980, p. 179-192, and Goldstein, *Pharmacol. Rev.* 18(1), 77 (1966), review DBH inhibitors.

Known inhibitors include, among others: picolinic acids, [See, Claxton et al., *Eur. J. Pharmacol.* 37, 179 (1976) and Runti et al., *Il. Farmaco Sci. Ed.* 36, 260 (1980)]; 2-(2-benzimidazolyl)amino-2-imidazoline dihydrochloride [See, Claxton, cited above]; and 1-alkyl-2-mercaptoimidazoles [See, Thorogood, European Patent Application No. 951 and Fuller et al., *Adv. Enzyme Regul.* 15, 267 (1976)].

DBH hydroxylates a variety of phenethylamine substrates. Rosenberg et al., "Essays in Neurochemistry and Neuropharmacology," Vol. 4, edit. by Youdim et al. John Wiley & Sons, 1980, pp. 163-209, extensively review the chemistry of DBH, including, at pp. 176-179 and 196-202, proposed mechanisms of action. There is not yet a known satisfactory model of the mechanism of action of DBH.

Although there are many known inhibitors of DBH, none of these agents has found clinical application because of non-specific, often toxic, properties they possess. Fusaric acid, for example, is hepatotoxic. See, for example, Teresawa et al., Japan, *Cir. J.* 35, 339 (1971) and references cited therein.

European Patent Application Publication No. 125783 discloses a series of imidazole derivatives having a phenylalkylene substituent in the 1-position and a carboxylic acid or aminomethyl moiety in the 2-position which inhibit DBH activity. In addition, European Patent Application Publication No. 125033 discloses a related series of 1-phenylalkylene imidazoles having a mercapto moiety in the 2-position.

Further, L'abbe et al., J. Org. Chem., 41, 1976, 1875 disclose the preparation of 1,4-disubstituted-5-mercaptotetrazoles from 1-benzyl-5-mercaptotetrazoles of structure:

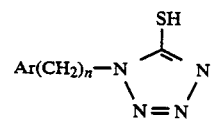

in which Ar is an unsubstituted phenyl group and n is 1. In addition, H. W. Altland, in J. Org. Chem., 41, 1976, 3395 discloses a number of 1-substituted-5-mercaptotetrazoles of the above structure in which Ar is an unsubstituted phenyl group and n is 1 or 2. No pharmaceutical use is disclosed for the compounds in either of the two foregoing references.

The present invention relates to 1-arylalkyl-2-mercaptotetrazole derivatives which have been found to inhibit dopamine-β-hyroxylase activity in mammals.

In one aspect of the invention, there is therefore provided novel compounds of structure (I),

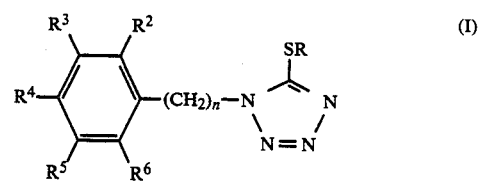

in which:

R is hydrogen or $C_{1-4}$ alkyl;

n is 1 to 5; and $R^2$ to $R^6$ are the same or different and are each hydrogen, halogen, hydroxy, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$-fluoroalkyl or $CO_2C_{1-4}$alkyl, provided that, when n is 1 or 2 and R is hydrogen, $R^2$ to $R^6$ are not all hydrogen;

or a pharmaceutically acceptable salt or hydrate thereof.

Suitably R is $C_{1-4}$ alkyl, for example, methyl. Preferably R is hydrogen.

Preferably n is 1 or 3.

Suitably, $R^2$, $R^3$, $R^5$ and $R^6$ are all hydrogen and $R^4$ is hydrogen, hydroxyl or $C_{1-4}$ alkoxy, for example methoxy. Preferably, two of $R^2$, $R^3$, $R^5$ and $R^6$ are halogen, for example chloro or fluoro, the other two are hydrogen and $R^4$ is hydrogen or hydroxy.

In particular, preferred compounds of structure (I) are, for example:

1-(3,5-difluorobenzyl)-5-mercaptotetrazole
1-(3,5-difluorobenzyl)-5-mercaptotetrazole
1-(2,6-dichlorobenzyl)-5-mercaptotetrazole
1-(4-methoxybenzyl)-5-mercaptotetrazole
1-(3-phenylpropyl)-5-mercaptotetrazole
1-(3-(3,5-difluorophenyl)propyl)-5-mercaptotetrazole
1-(3-(3,5-difluoro-4-methoxyphenyl)propyl)-5-mercaptotetrazole
1-(3-(3,5-dichlorophenyl)propyl)-5-mercaptotetrazole
1-(3-(4-methoxyphenyl)propyl)-5-mercaptotetrazole 1-(3-(4-hydroxyphenyl)propyl)-5-mercaptotetrazole
1-(3-(3,5-difluoro-4-hydroxyphenyl)propyl)-5-mercaptotetrazole In a further aspect of the invention there is provided pharmaceutical compositions comprising a compound of structure (II),

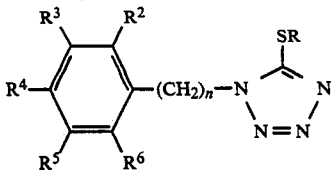

in which:
R is hydrogen or $C_{1-4}$ alkyl;
n is 1 to 5; and
$R^2$ to $R^6$ are the same or different and are each hydrogen, halogen, hydroxy, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$-fluoroalkyl or $CO_2C_{1-4}$alkyl;
or a pharmaceutically acceptable salt or hydrate thereof in association with a pharmaceutically acceptable carrier.

In a yet further aspect of the present invention there is provided a method of inhibiting dopamine-β-hydroxylase activity in mammals which comprises administering internally to a subject in need thereof an effective amount of a compound of structure (III),

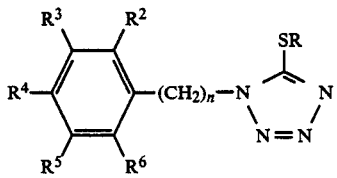

in which:
R is hydrogen or $C_{1-4}$alkyl;
n is 1 to 5;
$R^2$ to $R^6$ are the same or different and are each hydrogen, halogen, hydroxy, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$-fluoroalkyl or $CO_2C_{1-4}$alkyl;
or a pharmaceutically acceptable salt or hydrate thereof.

In a still further aspect of the present invention there is provided a process for the preparation of compounds of structure (I) which comprises:
(a) where R is hydrogen,
  (i) cyclization of a compound of structure (IV),

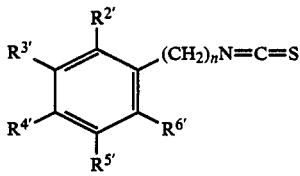

in which, n is 1 to 5 and $R^{2'}$ to $R^{6'}$ are selected from hydrogen, halogen, $C_{1-4}$ alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$fluoroalkyl or $CO_2C_{1-4}$alkyl; or
 (ii) cyclization of a compound of structure (VIII) and;

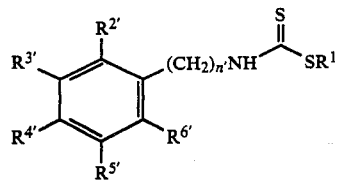

in which, n' is 1 to 5, $R^1$ is $C_{1-4}$ alkyl and $R^{2'}$ to $R^{6'}$ are selected from hydrogen, halogen, $C_{1-4}$alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$fluoroalkyl or $CO_2C_{1-4}$alkyl; or
(b) where R is $C_{1-4}$alkyl, alkylation of a compound of structure (I) in which R is hydrogen; and,
optionally converting a compound of structure (I) so formed into a pharmaceutically acceptable salt or hydrate.

In yet a further aspect of the present invention there are provided novel intermediates of structures (IV),

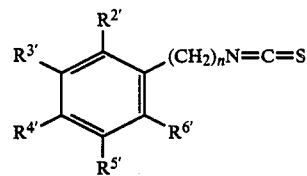

in which, n is 1 to 5 and $R^{2'}$ to $R^{6'}$ are selected from hydrogen, halogen, $C_{1-4}$alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$fluoroalkyl or $CO_2C_{1-4}$alkyl;
and compounds of structure (VIII),

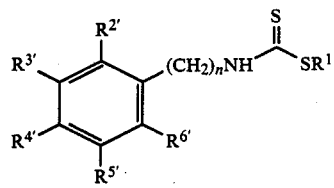

in which, n is 1 to 5, $R^1$ is $C_{1-4}$ alkyl and $R^{2'}$ to $R^{6'}$ are selected from hydrogen, halogen, $C_{1-4}$alkyl, CN, $NO_2$, $SO_2NH_2$, $CO_2H$, $CONH_2$, CHO, $CH_2OH$, $CF_3$, $C_{1-4}$alkoxy, $SO_2C_{1-4}$alkoxy, $SO_2C_{1-4}$fluoroalkyl or $CO_2C_{1-4}$alkyl; which are useful in the preparation of compounds of structure (I).

It is to be understood that the foregoing structures include the thione tautomers of compounds in which R is hydrogen i.e. compounds in which Y is =S.

Further it will be appreciated and understood by persons skilled in the art that due to free-rotation around the bond between the phenyl group and alkylene group substituents $R^2$ and $R^6$ and $R^3$ and $R^5$ are effectively equivalent.

The novel compounds of the present invention and compounds used in the compositions and methods of the invention can be prepared by methods analogous to those known in the art.

For example, compounds of structure (I) in which R is hydrogen can be prepared by (a) cyclization of a compound of structure (IV),

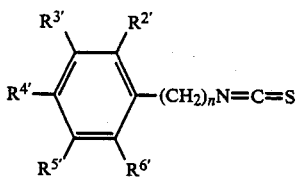

in which:

n is 1 to 5; and $R^{2'}$ and $R^{6'}$ are selected from hydrogen, halogen, $C_{1-4}$ alkyl, CN, $NO_2$, $SO_2NH_2$, $CO_2H$, $CONH_2$, CHO, $CH_2OH$, $CF_3$, $C_{1-4}$ alkoxy, $SO_2Cl_{1-4}$alkoxy, $SO_2C_{1-4}$fluoroalkyl or $CO_2C_{1-4}$ alkyl.

It is to be noted, and will be apparent to persons skilled in the art that the combination of substituents $R^{2'}$ to $R^{6'}$ (and of $R^2$ to $R^6$ in structures (I), (II) and (III) is limited to those combinations which are accessible and which do not result in significant instability due to steric hindrance.

The cyclization of intermediates (IV) to the desired compounds of structure (I) is carried out under aqueous conditions in the presence of sodium azide. Preferably, the reaction is carried out in water at reflux temperature.

The intermediates of structure IV are available in the art or can be prepared by methods well known to those skilled in the art for example, compounds of structure (IV) can be prepared from the corresponding precursor amines of structure (V),

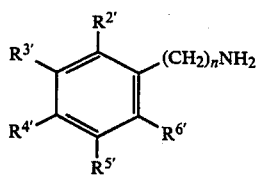

in which, n is 1 to 5; and $R^{2'}$ to $R^{6'}$ are as described for structure (IV). The reaction is carried out in the presence of thiophosgene at ambient temperature under basic conditions in an inert solvent. Suitable bases and solvents will be apparent to those skilled in the art, for example, triethylamine and tetrahydrofuran.

(b) cyclization of a compound of structure (VIII),

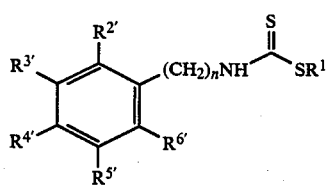

in which, n is 1 to 5, $R^1$ is $C_{1-4}$ alkyl and $R^{2'}$ to $R^{6'}$ are as described for structure (IV).

Suitable reaction conditions will be apparent to those skilled in the art, for example, at reflux under aqueous conditions in the presence of sodium azide.

Compounds of structure (VIII) can be prepared from compounds of structure (V), by reaction with, for example, carbon disulphide and a suitable iodoalkane under basic conditions, at reflux temperature of the solvent.

Preferably, the reaction is carried out in aqueous ethanolic potassium hydroxide solution in the presence of iodomethane to form a compound of structure (VI) in which $R^1$ is methyl.

The amines (V) can be prepared by methods well known in the art; for example, amines of structure (V) in which n is 3 to 5 can be prepared by reduction of the corresponding azides of structure (VA)

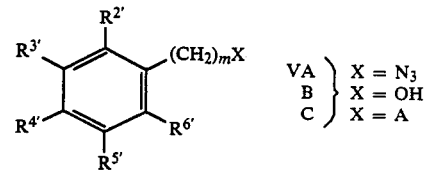

in which m=3 to 5 and $R^{2'}$ to $R^{6'}$ are as described for structure (V), using reagents known to those skilled in the art, for example hydrogenation in the presence of Raney nickel.

The azides of structure (VA) can be prepared from the corresponding compounds of structure (VB). Preferably, the compounds of structure (VB) are first activated by conversion to compounds of structure (VC) in which A is an activated group. Suitable activated groups will be apparent to those skilled in the art and include, the example o-tosyl and o-mesyl formed by reaction of compounds (VB) with p-toluenesulfonyl chloride and methanesulfonyl chloride respectively. Reaction of the intermediates of structure (VC) so formed with sodium azide in tetrahydrofuran gives the required azides (VA).

The intermediates of structure (VB) can be prepared from the corresponding acid derivatives of structure (VI),

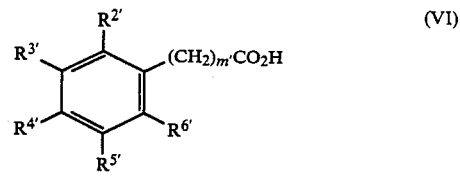

in which m' is 2 to 4; and $R^{2'}$ to $R^{6'}$ are as described for structure (IV).

Suitable reagents will be apparent to those skilled in art, for example, borane in tetrahydrofuran.

The compounds of structure (VI) can be prepared from the corresponding aldehyde precursors of structure (VII),

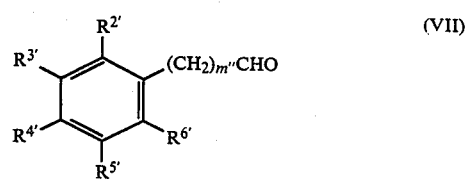

in which m'' is 0 to 2; and $R^{2'}$ to $R^{6'}$ are as described for structure (VII), by reaction, for example, where in structure (VI) m' is 2, with $CH_2(CO_2H)_2$ (malonic acid), in piperidine and pyridine at reflux temperature to give a compound of structure (VII) in which m'' is 2.

Alternatively, compounds of structure (V) in which n' is 1 to 5 can be prepared by reduction of the corresponding N-alkoxyimines of structure (IX):

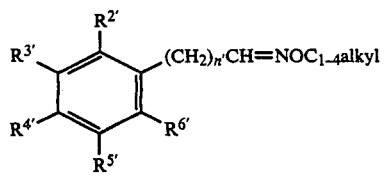
(IX)

in which n' is 0 to 4 and $R^{2'}$ to $R^{6'}$ are as described for structure (IV).

Suitable reaction conditions will be apparent to those skilled in the art for example, using borane in tetrahydrofuran.

The oxime intermediates of structure (IX) can be prepared from the corresponding aldehyde precursors of structure (X)

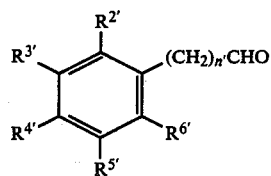
(X)

in which n' is 0 to 4 and $R^{2'}$ to $R^{6'}$ are as described in structure (IV), using an appropriate oxime, for example, methoxyamine in ethanol and pyridine at ambient temperature.

Compounds of structure (I) in which R is $C_{1-4}$ alkyl can be prepared from the corresponding compounds of structure (I) in which R is hydrogen, by, for example, alkylation in the presence of an alkylating agent in an inert solvent. Suitable alkylating agents include alkyl halides or tosylates and suitable inert solvents include, methanol, tetrahydrofuran and aqueous dimethylformamide. Preferred alkylating agents are alkyl iodides, for example, methyl iodide.

Where it is desired in the final product for a hydroxyl group to be present in one or more of $R^2$ to $R^6$, the corresponding O-alkyl compound is prepared and the alkyl group then removed to give the free OH group. Preferably, the foregoing reactions are performed on the O-methyl ethers which are deprotected using any one of the number of reagents known in the art, for example, $AlCl_3$, $BBr_3$, HBr in water or acetic acid, hydrogen iodide or methanesulfonic acid with or without methionine.

The pharmaceutically acceptable acid addition salts of the compounds wherein R is $C_{1-4}$ alkyl, are formed with strong or moderately strong organic or inorganic acids by methods known in the art. For example, the base is reacted with an inorganic or organic acid in an aqueous miscible solvent such as ethanol with isolation of the salt by removing the solvent or an an aqueous immiscible solvent when the acid is soluble therein, such as ethyl ether or chloroform, with the desired salt separating directly or being isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

The compounds of the invention and the compounds used in the method and pharmaceutical composition of the invention, because they can be used to inhibit DBH activity, have therapeutic value as diuretic, natriuretic, cardiotonic, antihypertensive and vasodilator agents, as well as antiulcerogenic and anti-parakinsonism agents. An advantageous feature of the compounds is their high degree of lipophilicity. This feature increases in vivo potency by facilitating transport into adrenergic neurons.

Compounds of the invention and other compounds useful in the method of the invention were screened for in vitro DBH inhibition by a standard procedure for assaying conversion of tyramine to octopamine in the presence of DBH. Octopamine was assayed following sodium periodate oxidation to p-hydroxybenzaldehyde by measuring spectrophotometric absorbance at 330 nm. Results are given in Table I, below. Inhibition is given in molar concentration of compounds at which DBH activity was halved ($IC_{50}$). Melting points (mp) are given in °C. By this procedure fusaric acid has an $IC_{50}$ of about $8 \times 10^{-7}$.

TABLE 1

| Example No. | $IC_{50}$ (M) |
| --- | --- |
| 1 | $1.5 \times 10^{-6}$ |
| 2 | $1.0 \times 10^{-6}$ |
| 3 | $9.2 \times 10^{-6}$ |
| 4 | $1.5 \times 10^{-5}$ |
| 5 | $2.4 \times 10^{-6}$ |
| 6 | $1.3 \times 10^{-5}$ |
| 7 | $3.5 \times 10^{-7}$ |
| 9 | $3.9 \times 10^{-7}$ |
| 11 | $7.9 \times 10^{-7}$ |
| 12 | $8.0 \times 10^{-8}$ |

Various compounds of the invention were tested for their effects in vivo on peripheral dopamine (DA) and norepinephrine (NE) levels substantially by the procedure of DaPrada and Zürcher, Life Sci., 19, 1161, (1976). Spontaneously hypertensive rats were dosed twice, the second dose being about 18 hours after the first, and were sacrificed about 2 hours after the second dose. Averaged results, expressed in micrograms of DA and NE per gram of tissue are given in Table II.

TABLE II

| Compound | No. of Animals | DA ug/g | NE ug/g | DA/NE Ratio |
| --- | --- | --- | --- | --- |
| Control ($H_2O$) | | $0.282 \pm 0.034$ | $7.737 \pm 0.637$ | $0.036 \pm 0.002$ |
| Example 2 | | $0.360 \pm 0.015$ | $6.838 \pm 0.257$ | $0.053 \pm 0.0035$ |

Further, the same rats were dosed with a suspension or solution at a dose of 50 mg/kg of test compound i.p. and mean arterial blood pressure was determined with indwelling cannulae inserted into the tail artery. A significant reduction in mean arterial pressure was recorded in rats dosed with 50 mg/kg, ip, of the compounds of examples 2 and 6.

The compounds can be incorporated into convenient dosage unit forms such as capsules, tablets or injectable preparations. Pharmaceutical carriers which can be employed can be solid or liquid. Solid carriers include, among others, lactose, terra alba, sucrose, talc, gelatin, agar, pectin, acacia, magnesium stearate, and stearic acid. Liquid carriers include, among others, syrup, peanut oil, olive oil and water. Similarly, the carrier or diluent may include any time delay material, such as glyceryl monostearate or glyceryl distearate, along or with a wax. The amount of solid carrier will vary widely but, preferably, will be from about 25 mg to about 1 g per dosage unit. If a liquid carrier is used, the preparation will be in the form of a syrup, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating and compressing, when necessary, for tablet forms, or mixing, filling and dissolving the ingredients, as appropriate, to give the desired oral or parenteral products.

Doses of the present compounds in a pharmaceutical dosage unit will be an effective amount, that is, a nontoxic quantity selected from the range of 0.1–1000 mg/kg of active compound, preferably 10–100 mg/kg. The selected dose is administered to a patient in need of treatment from 1–5 times daily, orally, rectally, by injection or by infusion. Parenteral administration, which uses a low dose, is preferred. However, oral administration, at a higher dose, can also be used when safe and convenient for the patient.

The following examples are illustrative of preparation of compounds of the invention or intermediates thereof. The starting compounds of Examples 1, 4E, 4F, 8 and 9 are commercially available or are prepared by known techniques. The Examples are not intended to limit the scope of the invention as defined hereinabout and as claimed below. The compounds listed in Tables I and II, above, were prepared substantially by the illustrated procedures. All temperatures and melting points (mp) are in degrees Celsius (°C.).

EXAMPLE 1

1-(3,5-Difluorobenzyl)-5-mercaptotetrazole

A: 3,5-Difluorobenzylamine

A solution of 3,5-difluorobenzonitrile (0.0345 mol) in ammonia saturated methanol (100 ml) and methanol washed Raney nickel were shaken together under 50 psi of hydrogen for 1½ hours. The reaction mixture was filtered, the filtrate concentrated then dissolved in ethyl acetate. The product was extracted into 3N aqueous hydrogen chloride. The acidic solution was cooled and basified with 50% sodium hydroxide then was extracted into ethyl acetate. The organic extract was dried over sodium sulfate, filtered and concentrated to yield 4.3 g (86%) yellow oil.

B: Methyl N-(3,5-difluorobenzyl)dithiocarbamate

Carbon disulfide (0.148 mol) was added to a solution of 3,5-difluorobenzylamine (0.0297 mol) and potassium hydroxide (0.0297 mol) in water (20 ml) and ethanol (18 ml). The reaction was refluxed one hour then was cooled and iodomethane (0.0297 mol) was added. After stirring at 25° for 48 hours, the reaction mixture was concentrated, suspended in ethyl acetate, washed with water, dried over sodium sulfate and reconcentrated. The crude product was chromatographed on silica gel, eluting with 6:1 hexane/ethyl acetate, to yield 4.7 g (68%) white needles: mp 53°–54° (hexane).

C: 1-(3,5-Difluorobenzyl)-5-mercaptotetrazole

Methyl N-(3,5-difluorobenzyl)dithiocarbamate (0.018 mol) and sodium azide (0.027 mol) were refluxed in water (35 ml) for 18 hours. The reaction was cooled and washed with ethyl acetate. The aqueous phase was acidified with 3N aqueous hydrogen chloride, extracted into ethyl acetate, dried over sodium sulfate and concentrated to yield 2.5 g (61%) white crystals: mp 155°–156° (ethyl acetate/hexane).

EXAMPLE 2

Preparation of 1-(3,5-Dichlorobenzyl)-5-mercapto-tetrazole

A: O-Methyl-3,5-dichlorobenzaldoxime

A solution of 3,5-dichlorobenzaldehyde (0.0571 mol) and methoxyamine hydrochloride (0.0629 mol) in ethanol (50 ml) and pyridine (50 ml) was stirred 18 hours at room temperature. The reaction was concentrated and partitioned between methylene chloride and water. The organic phase was washed with 3N aqueous hydrogen chloride, dried over sodium sulfate and was concentrated to yield 10.9 g (94%) white solid, mp 53°.

B: 3,5-Dichlorobenzylamine

Borane-tetrahydrofuran complex, 1 molar in tetrahydrofuran (0.054 mol) was added to a cooled (0°, ice/water) solution of O-methyl-3,5-dichlorobenzaldoxime (0.0493 mol) in dry tetrahydrofuran (50 ml). The reaction was refluxed 2 hours, then was cooled, water (20 ml) followed by 10% aqueous sodium hydroxide (20 ml) were carefully added, and the reaction was refluxed an additional 2 hours. After cooling, the phases were separated. The aqueous phase was extracted with ether, then the combined organic phases were extracted into 3N hydrogen chloride. The acidic solution was cooled and basified with 50% aqueous sodium hydroxide and extracted into ether. After drying over sodium sulfate and concentrating, 5.34 g (62%) of yellow oil was obtained.

C: Methyl N-(3,5-Dichlorobenzyl)dithiocarbonate 3,5-Dichlorobenzylamine (0.030 mol) was allowed to react with carbon disulfide (0.150 mol) and iodomethane (0.030 mol) substantially as described in Example 1B above to obtain 3.6 g (45%) white needles: mp 88°–89° (hexane).

D: 1-(3,5-Dichlorobenzyl)-5-mercaptotetrazole

Methyl N-(3,5-dichlorobenzyl)dithiocarbamate (0.0109 mol) and sodium azide (0.016 mol) were reacted substantially as described in Example 1C above to obtain 1.5 g (53%) white crystals: mp 152°–153° (ethyl acetate/hexane).

EXAMPLE 3

1-(2,6-Dichlorobenzyl)-5-mercaptotetrazole

A: N-Methoxy-2,6-dichlorobenzylimine 2,6-Dichlorobenzaldehyde (0.057 mol) and methoxyamine hydrochloride were reacted substantially as described in Example 2A above to yield 10.8 g (93%) of a low melting solid.

B: 2,6-Dichlorobenzylamine

N-Methoxy-2,6-dichlorobenzylimine (0.049 mol) and boran-tetrahydrofuran complex (0.050 mol) were reacted substantially as described in Example 2B above to yield 7 g (82%).

C: Methyl N-(2,6-dichlorobenzyl)dithiocarbamate 2,6-Dichlorobenzylamine (0.020 mol) was reacted with carbon disulfide (0.020 mol) and iodomethane (0.019 mol) substantially as described in Example 1B above to obtain 1.5 g (32%) white crystals: mp 47°.

D: 1-(2,6-Dichlorobenzyl)-5-mercaptotetrazole

Methyl N-(2,6-dichlorobenzyl)dithiocarbomate (0.006 mol) and sodium azide (0.0085 mol) were reacted substantially as described in Example 1C to yield 0.25 g (16%) white crystals: mp 197°–198° (ethyl ether).

EXAMPLE 4

1-(4-Methoxybenzyl)-5-mercaptotetrazole

A: Methyl N-(4-Methoxybenzyl)dithiocarbamate

4-Methoxybenzylamine (0.073 mol) was reacted with carbon disulfide (0.073 mol) and iodomethane (0.073 mol) substantially as described in Example 1B above to obtain 7.2 g (43%) as a crystalline solid: mp 67°–70°.

B: 1-(4-Methoxybenzyl)-5-mercaptotetrazole

Methyl N-(4-methoxybenzyl)dithiocarbamate (0.0317 mol) and sodium azide (0.043 mol) were reacted substantially as described in Example 1C above to obtain 3.3 g (47%) white crystals: mp 163°–165° (ethyl ether).

EXAMPLE 5

1-(3-Phenylpropyl)-5-mercaptotetrazole

A: Methyl N-(3-phenylpropyl)dithiocarbamate

3-Phenyl-1-propylamine (0.074 mol) was reacted with carbon disulfide (0.074 mol) and iodomethane (0.074 mol) substantially as described in Example 1B above to obtain 15.7 g (94%) of a yellow oil.

B: 1-(3-Phenylpropyl)-5-mercaptotetrazole

Methyl N-(3-phenylpropyl)dithiocarbamate (0.044 mol) and sodium azide (0.062 mol) were reacted substantially as described in Example 1C above to obtain 2.0 g (21%) colorless crystals: mp 75°–76° (pet. ether).

EXAMPLE 6

1-Benzyl-5-mercaptotetrazole

Benzyl isothiocyanate (0.020 mol) and sodium azide (0.030 mol) were reacted substantially as described in Example 1C above to yield 0.27 g (7%) white needles: mp 141°–142° (chloroform/pet. ether).

EXAMPLE 7

1-(3-(3,5-Difluorophenyl)propyl-5-mercaptotetrazole

A: 3,5-Difluorobenzaldehyde

A mixture of 3,5-difluorobenzonitrile (0.108 mol) and Raney alloy (15 g) was refluxed 2 hours in 90% formic acid (150 ml). The reaction was filtered hot and the filter cake was washed with water, then hexane. The filtrate was extracted three times with hexane, the combined hexane extracts were washed with water and dried over sodium sulfate. Concentration yielded 8.4 g (55%) of a yellow oil.

B: 3-(3,5-Difluorophenyl)propenoic acid 3,5-Difluorobenzaldehyde (0.058 mol), malonic acid (0.0877 mol), pyridine (0.041 mol) and piperidine (0.0015 mol) were heated 2 hours on a steam bath, then 1 hour at 155°. Cold 3N aqueous hydrogen chloride was added and the product filtered. The crude product was recrystallized from ethanol to yield 8 g (75%) white crystals: mp 199°–200° (ethanol).

C: 3-(3,5-Difluorophenyl)propanoic acid

A solution of 3-(3,5-difluorophenyl)propenoic acid (0.0435 mol) in tetrahydrofuran (100 ml) and a slurry of 10% palladium on carbon (1.5 g) in ethyl acetate were shaken together under 50 psi hydrogen for 4 hours. The mixture was filtered and concentrated to yield 8 g (99%) of a yellow oil.

D: 3-(3,5-Difluorophenyl)propanol

Borane-tetrahydrofuran complex (0.095 mol) was added to a cooled (0°) solution of 3-(3,5-difluorophenyl)propanoic acid (0.043 mol) in tetrahydrofuran (75 ml). The reaction was stirred 2 hours at room temperature, then methanol was carefully added and the reaction was concentrated. The crude product was dissolved in ethyl ether, washed with water, dried over sodium sulfate and concentrated to yield 7 g (95%) of an oily product.

E: 3-(3,5-Difluorophenyl)propyl azide

Tosyl chloride (0.0814 mol) was added to a cooled (0°) solution of 3-(3,5-difluorophenyl)propanol (0.0407 mol) in pyridine (75 ml). The reaction was stirred 2 hours at 25°, then it was poured into ice/water and extracted into ethyl ether. The ethereal extracts were washed with 3N aqueous hydrogen chloride and water, then were dried over sodium sulfate and concentrated. The residue was dissolved in dimethylformamide (75 ml) and sodium azide (0.0814 mol) was added. The reaction was stirred 8 hours, then was diluted with water and extracted into ethyl acetate. The organic extract was washed with 3N aqueous hydrogen chloride and water, then dried over sodium sulfate and concentrated to yield 6.7 g (64%) of an oily product.

F: 3-(3,5-Difluorophenyl)propylamine 3-(3,5-Difluorophenyl)propylazide (0.034 mol) in methanol (75 ml) was shaken with a slurry of methanol washed Raney nickel under 50 psi hydrogen for 2 hours. The reaction mixture was filtered and the filtrate concentrated to yield 5.6 g (96%) of an oily product.

G: 3-(3,5-Difluorophenyl)propyl Isothiocyanate

A solution of 3-(3,5-difluorophenyl)propylamine (0.0327 mol) and triethylamine (0.072 mol) in tetrahydrofuran (20 ml) was added dropwise to a solution of thiophosgene (0.0392 mol) in tetrahydrofuran at 0°. The reaction was stirred 2 hours at room temperature then ethyl ether was added and the mixture filtered. The filtrate was concentrated and distilled (Kugelrohr) to yield 3.8 g (55%) of a yellow oil.

H: 1-(3-(3,5-Difluorophenyl)propyl)-5-mercaptotetrazole

To a solution of 3-(3,5-difluorophenyl)propyl isothiocyanate (0.0177 mol) in dimethylformamide (35 ml) was added water (12 ml), followed by sodium azide (0.0361 mol). The reaction was stirred one hour, then it was diluted with water and washed with ethyl acetate. The aqueous phase was acidified with 3N aqueous hydrogen chloride, extracted into ethyl acetate, washed with water, dried over sodium sulfate and was concentrated. The residue was dissolved in ethyl ether and dicyclohexylamine (1.9 ml) was added. The resulting salt was filtered and partitioned, with stirring, between ethyl ether and 3N aqueous hydrogen chloride. The ethereal layer was washed with water, dried over sodium sulfate and concentrated. The crude product was recrystallized from pet. ether to yield 1.2 g (27%) white crystals: mp 80°-81° (pet. ether).

EXAMPLE 8

1-(3-(3,5-Difluoro-4-methoxyphenyl)propyl)-5-mercaptotetrazole

A: 3,5-Difluoro-4-methoxybenzaldehyde 3,5-Difluoro-4-methoxybenzonitrile (0.237 mol), Raney alloy (40 g) and 90% formic acid (400 ml) were reacted substantially as described in Example 7A above to obtain 22.9 g (56%) of a white, low melting solid.

B: 3-(3,5-Difluoro-4-methoxyphenyl)propenoic acid 3,5-Difluoro-4-methoxybenzaldehyde (0.131 mol), malonic acid (0.196 mol), pyridine (0.0989 mol) and piperidine (0.004 mol) were reacted substantially as described in Example 7B above to obtain 16.8 g (55%) of white crystals: mp 211° (ethanol).

C: 3-(3,5-Difluoro-4-methoxyphenyl)propanoic acid

A solution of 3-(3,5-difluoro-4-methoxyphenyl)-propenoic acid (0.078 mol) in tetrahydrofuran (100 ml) and a slurry of 10% palladium on carbon (2 g) in ethyl acetate were reacted substantially as described in Example 7C above to obtain 16.7 g (99%), white crystals: mp 72°-73°.

D: 3-(3,5-Difluoro-4-methoxyphenyl)propanol 3-(3,5-Difluoro-4-methoxyphenyl)propanoic acid (0.074 mol) and borane-tetrahydrofuran complex (0.165 mol) were reacted substantially as described in Example 7D above to give 14.6 g (99%) clear oil.

E: 3-(3,5-Difluoro-4-methoxyphenyl)propyl azide 3-(3,5-Difluoro-4-methoxyphenyl)propanol (0.073 mol), tosyl chloride (0.146 mol) and sodium azide (0.146 mol) were reacted substantially as described in Example 7E above to obtain 15.6 g (95%) yellow oil.

F: 3-(3,5-Difluoro-4-methoxyphenyl)propylamine 2-(3,5-Difluoro-4-methoxyphenyl)propylazide (0.0693 mol) was reacted with Raney nickel substantially as described in Example 7F above to obtain 14 g (102%) of an oily product.

G: 3-(3,5-Difluoro-4-methoxyphenyl)propylisothiocyanate 3-(3,5-Difluoro-4-methoxyphenyl)propylamine (0.0693 mol), triethylamine (0.152 mol) and thiophosgene (0.076 mol) were reacted substantially as described in Example 7G to obtain 8.8 g (53%) of a yellow oil.

H: 1-(3-(3,5-Difluoro-4-methoxyphenyl)propyl-5-mercaptotetrazole 3-(3,5-Difluoro-4-methoxyphenyl)propylisothiocyanate (0.036 mol) and sodium azide (0.054 mol) were reacted substantially as described in Example 7H above to give 4 g (39%) white crystals: mp 64°-65°.

EXAMPLE 9

1-(3-(3,5-Dichlorophenyl)propyl)-5-mercaptotetrazole

A: 3-(3,5-Dichlorophenyl)propenoic acid 3,5-Dichlorobenzaldehyde (0.154 mol), malonic acid (0.232 mol), pyridine (0.0989 mol) and piperidine (0.004 mol) were reacted substantially as described in Example 7B above to obtain 22.9 g (69%) white crystals: mp 171°-172° (ethanol)

B: 3-(3,5-Dichlorophenyl)propanoic acid

A: 3-(3,5-Dichlorophenyl)propenoic acid (0.106 mol) and 10% palladium on carbon (3 g) were reacted substantially as described in Example 7C above to obtain 23 g (100%) yellow oil.

C: 3-(3,5-Dichlorophenyl)propanol 3-(3,5-Dichlorophenyl)propanoic acid (0.106 mol) and borane-tetrahydrofuran complex (0.233 mol) were allowed to react substantially as described in Example 7D above to obtain 21.2 g (98%) of a colorless oil.

D: 3-(3,5-Dichlorophenyl)propyl azide 3-(3,5-Dichlorophenyl)propanol (0.052 mol), tosyl chloride (0.104 mol) and sodium azide (0.104 mol) were reacted substantially as described in Example 7E to obtain 11.7 g (98%) of an oily product.

E: 3-(3,5-Dichlorophenyl)propylamine 3-(3,5-Dichlorophenyl)propylazide (0.0506 mol) was reacted with Raney nickel substantially as described in Example 7F above to obtain 10.4 g (100%) of an oily product.

F: 1-(3-(3,5-Dichlorophenyl)propyl)isothiocyanate 3-(3,5-Dichlorophenyl)propylamine (0.049 mol), triethylamine (0.108 mol) and thiophosgene (0.0542 mol) were reacted substantially as described in Example 7G above to give 6.4 g (53%) of a yellow oil.

G: 1-(3-(3,5-Dichlorophenyl)propyl)-5-mercaptotetrazole 1-(3-(3,5-Dichlorophenyl)propylisothiocyanate (0.0253 mol) and sodium azide (0.0385 mol) were reacted substantially as described in Example 7H above to give 1.7 g (23%) of white crystals: mp 119° (ethyl acetate-hexane).

EXAMPLE 10

1-(3-(4-Methoxyphenyl)propyl)-5-mercaptotetrazole

A: 3-(4-Methoxyphenyl)propylamine

Lithium aluminium hydride (0.01 mol) and tetrahydrofuran (500 ml) were placed in a 1 liter flask fitted with a soxhlet extractor, with 3-(4-methoxyphenyl)-propanamide (0.056 mol) in the extraction thimble. The reaction was refluxed 3 hours, was cooled and water (3.5 ml) was carefully added. After the mixture was sequentially extracted with 10% aqueous sodium hydroxide (3.5 ml) and water (10.5 ml), the mixture was filtered and concentrated. The crude product was distilled (Kugelrohr) to yield 4.4 g (48%) of a colorless oil which was stored under $N_2$.

B: 3-(4-Methoxyphenyl)propylisothiocyanate 2-(4-Methoxyphenyl)propylamine (0.027 mol), triethyl amine (0.0594 mol) and thiophosgene (0.0297 mmol) were reacted substantially as described in Example 7G to obtain 3.6 g (64%) of a yellow oil.

C: 1-(3-(4-Methoxyphenyl)propyl)-5-mercaptotetrazole 3-(4-Methoxyphenyl)propylisothiocyanate (0.0174 mol) and sodium azide (0.0261 mol) were reacted substantially as described in Example 7H to give 2.4 g (55%) of an orange oil.

EXAMPLE 11

1-(3-(4-Hydroxyphenyl)propyl)-5-mercaptotetrazole 1-(3-(4-Methoxyphenyl)propyl)-5-mercaptotetrazole (0.0072 mol) was refluxed in acetic acid saturated with hydrogen bromide (75 ml) for 2 hours. The reaction mixture was concentrated and the residue was flash chromatographed on silica gel, eluting with 5% methanol in methylene chloride. The chromatographed material was recrystallized from water to yield 0.168 g (9.9%) colorless crystals: m.p. 145°–146° (water).

EXAMPLE 12

1-(3-(3,5-Difluoro-4-hydroxyphenyl)propyl)-5-mercaptotetrazole 1-(3-(3,5-Difluoro-4-methoxyphenyl)propyl)-5-mercaptotetrazole (0.014 mol) was refluxed 4 hours in acetic acid saturated with hydrogen bromide (100 ml). The reaction mixture was concentrated, the residue was taken up in ethyl ether and dicyclohexylamine (2.8 ml) was added. The resulting salt was filtered and partitioned between ethyl ether and 3N aqueous hydrogen chloride. The ethereal layer was washed with water, dried over sodium sulfate and concentrated. The crude product was dissolved in hot water, filtered, acidified with 3N aqueous hydrogen chloride and extracted into ethyl ether. The ethereal solution was dried over sodium sulfate and concentrated to yield 0.86 g (22%) of white crystals: mp 87° (ethyl acetate/hexane).

EXAMPLES 13–34

The compounds shown in Table III are prepared substantially by the procedures illustrated above, except that suitable molar amounts of appropriate starting materials and other reagents are used.

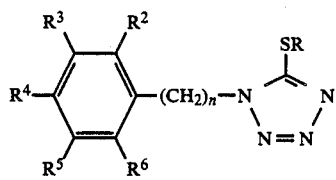

(I)

| | R | $R_2$ | $R_3$ | $R_4$ | $R_5$ | $R_6$ | n |
|---|---|---|---|---|---|---|---|
| 13 | H | Cl | H | H | H | H | 1 |
| 14 | H | Cl | Cl | Cl | H | H | 1 |
| 15 | H | F | Cl | H | H | H | 1 |
| 16 | H | HO | F | H | H | H | 2 |
| 17 | H | H | H | HO | H | H | 2 |
| 18 | H | H | F | HO | F | H | 2 |
| 19 | H | H | Cl | HO | Cl | H | 2 |
| 20 | $CH_3$ | H | Cl | HO | Cl | H | 2 |
| 21 | $CH_3$ | H | F | HO | F | H | 2 |
| 22 | $CH_3$ | H | F | H | F | H | 2 |
| 23 | H | H | F | H | F | H | 4 |
| 24 | H | H | F | H | F | H | 5 |
| 25 | H | H | F | HO | F | H | 4 |
| 26 | H | H | F | HO | F | H | 5 |
| 27 | $CH_3$ | H | F | HO | F | H | 4 |
| 28 | $CH_3$ | H | Cl | HO | Cl | H | 5 |

-continued

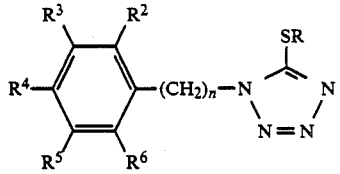

(I)

| | R | $R_2$ | $R_3$ | $R_4$ | $R_5$ | $R_6$ | n |
|---|---|---|---|---|---|---|---|
| 29 | H | H | Cl | HO | F | H | 3 |
| 30 | H | H | Cl | H | F | H | 3 |
| 31 | H | H | Cl | H | F | H | 1 |
| 32 | $CH_3$ | H | Cl | H | F | H | 1 |
| 33 | $CH_3$ | H | Cl | H | F | H | 3 |
| 34 | $CH_3CH_2$ | H | Cl | H | F | H | 1 |

EXAMPLE 35

The ingredients in Table IV are screened, mixed and filled into a hard gelatin capsule.

TABLE IV

| Ingredients | Amounts |
|---|---|
| 1-(3,5-Dichlorobenzyl)-5-mercaptotetrazole (compound of Example 2). | 50 mg |
| magnesium stearate | 5 mg |
| lactose | 75 mg |

EXAMPLE 36

The sucrose, calcium sulfate dihydrate and compound shown in Table V are mixed and granulated with a 10% gelatin solution. The wet granules are screened, dried, mixed with the starch, talc and stearic acid, screened and compressed into a tablet.

TABLE V

| Ingredients | Amounts |
|---|---|
| 1-(3,5-dichlorobenzyl)-5-mercaptotetrazole | 100 mg |
| calcium sulfate dihydrate | 150 mg |
| sucrose | 20 mg |
| starch | 10 mg |
| talc | 5 mg |
| stearic acid | 3 mg |

EXAMPLE 37

1-(3,5-dichlorobenzyl)-5-mercaptotetrazole (75 mg) is suspended in 25 ml of normal saline to give an injectable preparation.

What we claim is:

1. A compound of structure (VIII)

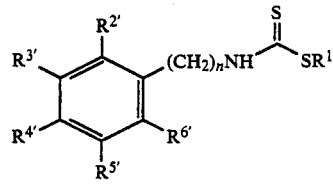

(VIII)

in which, n is 1 to 5, $R^1$ is $C_{1-4}$ alkyl and two of $R^{2'}$, $R^{3'}$, $R^{5'}$ and $R^{6'}$ are halogen and the other two are hydrogen and $R^{4'}$ is hydrogen or hydroxy.

2. A compound as claimed in claim 1 which is methyl N-(3,5-difluorobenzyl)dithiocarbamate.

3. A compound as claimed in claim 1 which is methyl N-(3,5-dichlorobenzyl)dithiocarbamate.

4. A compound as claimed in claim 1 which is methyl N-(2,6-dichlorobenzyl)dithiocarbamate.

* * * * *